United States Patent
Banowski et al.

(10) Patent No.: US 11,090,237 B2
(45) Date of Patent: Aug. 17, 2021

(54) DEODORANT COSMETIC COMPOSITIONS COMPRISING CALCIUM SILICATE AND SODIUM BICARBONATE

(71) Applicant: Henkel AG & Co. KGaA, Duesseldorf (DE)

(72) Inventors: Bernhard Banowski, Duesseldorf (DE); Marcus Claas, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/680,910

(22) Filed: Nov. 12, 2019

(65) Prior Publication Data

US 2020/0170901 A1    Jun. 4, 2020

(30) Foreign Application Priority Data

Dec. 4, 2018 (DE) .............. 102018220966

(51) Int. Cl.
| | | |
|---|---|---|
| *A61K 8/25* | (2006.01) | |
| *A61K 8/19* | (2006.01) | |
| *A61K 8/02* | (2006.01) | |
| *A61K 8/73* | (2006.01) | |
| *A61K 8/92* | (2006.01) | |
| *A61Q 15/00* | (2006.01) | |
| *A61K 8/26* | (2006.01) | |

(52) U.S. Cl.
CPC .............. *A61K 8/25* (2013.01); *A61K 8/0241* (2013.01); *A61K 8/19* (2013.01); *A61K 8/26* (2013.01); *A61K 8/732* (2013.01); *A61K 8/922* (2013.01); *A61Q 15/00* (2013.01)

(58) Field of Classification Search
CPC ........ A61Q 19/00; A61Q 15/00; A61Q 17/04; A61Q 19/08; A61Q 17/005; A61Q 19/10; A61Q 1/02; A61Q 1/06; A61Q 5/02; A61Q 11/00; A61Q 19/007; A61Q 3/00; A61Q 9/02; A61Q 5/065; A61Q 5/10; A61Q 5/12; A61Q 13/00; A61Q 19/002; A61Q 1/14; A61Q 5/006; A61Q 5/06; A61K 8/25; A61K 8/0241; A61K 8/19; A61K 8/26; A61K 8/732; A61K 8/922
See application file for complete search history.

(56) References Cited

U.S. PATENT DOCUMENTS

| | | |
|---|---|---|
| 2003/0059387 A1 | 3/2003 | Bergquist |
| 2013/0280175 A1 | 10/2013 | Banowski et al. |
| 2018/0168954 A1 * | 6/2018 | Millet .................... A61K 8/922 |

FOREIGN PATENT DOCUMENTS

| | | |
|---|---|---|
| DE | 10 2010 055 816 A1 | 6/2012 |
| DE | 10 2010 063 250 A1 | 6/2012 |
| DE | 10 2012 222 692 A1 | 9/2013 |
| JP | 2009138124 A | 6/2009 |
| JP | 2016108330 A | 6/2016 |
| JP | 2016141637 A | 8/2016 |
| WO | 9856340 A1 | 12/1998 |
| WO | WO-0035413 A1 * | 6/2000 ............... A61K 8/87 |

OTHER PUBLICATIONS

EWG's Skin Deep, Purelygreat Tea Tree Natural Deodorant, Nov. 2017, Environmental Working Group, from https://www.ewg.org/skindeep/products/761964-Purelygreat_Tea_Tree_Natural_Deodorant/ (Year: 2017).*

Lisalise-Natural Skin Care, No. Sweat—The basic makeup of deodorant, Sep. 2012, from https://www.lisaliseblog.com/2012/02/no-sweat-basic-makeup-of-deodorant.html (Year: 2012).*

* cited by examiner

*Primary Examiner* — Bethany P Barham
*Assistant Examiner* — Ayaan A Alam
(74) *Attorney, Agent, or Firm* — Lorenz & Kopf, LLP

(57) ABSTRACT

The present disclosure relates to deodorant cosmetic compositions including calcium silicate and baking soda. Furthermore, the present disclosure relates to a cosmetic product containing such compositions and the use of the compositions or products for reduction of the body odor released by perspiration.

4 Claims, No Drawings

DEODORANT COSMETIC COMPOSITIONS COMPRISING CALCIUM SILICATE AND SODIUM BICARBONATE

CROSS-REFERENCE TO RELATED APPLICATION

This application claims priority to German Patent Application No. 10 2018 220 966.9, filed Dec. 4, 2018, which is incorporated herein by reference in its entirety.

TECHNICAL FIELD

The present disclosure relates to deodorant compositions including calcium silicate and sodium bicarbonate.

BACKGROUND

Washing, cleaning and care for the body are a basic human need and modern industry continuously attempts to meet these human needs in a variety of ways. Long-lasting elimination or at least reduction of the body odor and underarm wetness are especially important for daily hygiene. Numerous deodorizing or antiperspirant personal care products are known in the prior art, which were developed for use in body regions with a high density of sweat glands, particularly in the underarm region. They are assembled in a wide variety of dosage forms, such as a powder, stick form, aerosol spray, pump spray, liquid and gel-like roll-on application, lotion, gel and as a moist flexible substrate (deodorant wipes).

A distinction is made between the so-called apocrine and eccrine sweat glands. Apocrine sweat glands secrete an oily, emulsion-like sweat, which contains ingredients that are responsible for the development of body odour. Body odour results to a large extent from the bacterial decomposition of individual components of apocrine sweat on the skin. With the help of enzymes, various bacterial species transform non-smelling ingredients of sweat into volatile, strongly smelling, organic compounds, e.g. short-chain, linear and/or branched, saturated and/or unsaturated fatty acids, sulphanyl alcohols, steroid degradation products and other components.

In body deodorization, a general distinction can be made between active substances that absorb unpleasant smelling substances that have already formed (activated carbon, zinc cicinoleate, cyclodextrins, ion exchangers) or hinder perception by the olfactory receptors (perfumes, perfumes) and active substances that prevent or at least slow down the decomposition of sweat and the development of unpleasant smelling substances (antibacterial, germ-inhibiting active substances, prebiotically/prebiotically active components i.e. active substances influencing the germ flora, as well as enzyme inhibitors). Depending on the mechanism chosen to prevent body odour, odour absorbers, fragrances, deodorizing ion exchangers, germ inhibitors, prebiotic/prebiotic components, enzyme inhibitors and other active substances can be used as cosmetic deodorizing agents. The active substances must be contained in the compositions, ensuring that the compositions can be conveniently provided in a desired dosage form and that the compositions do not cause an unpleasant feeling on the skin.

Eccrine sweat glands secrete a high amount of aqueous secretion, which is perceived as unpleasant because of the formation of wet spots on the clothing. Eccrine sweating can be reduced by narrowing the sweat channels, e.g. by aluminum salts or by biologically active substances that regulate the function of the gland.

The state-of-the-art cosmetic antiperspirants used to inhibit perspiration contain aluminum and/or zirconium compounds as deodorant and/or antiperspirant active ingredients. These deodorizing and/or antiperspirant compounds reduce the sweat secretion of the body by temporarily narrowing and/or clogging the excretory ducts of the sweat glands, so that the amount of sweat can be reduced by from about 20 to about 60 percent. On the other hand, they have an additional deodorizing effect due to their antimicrobial effect. However, the aluminum and/or zirconium compounds used to inhibit perspiration can cause unpleasant skin reactions in some users. Aluminum compounds in particular are regarded as critical by consumers. Furthermore, the use of the deodorizing and/or antiperspirant compounds can lead to staining on clothing.

Efforts have been made in the prior art to formulate aluminum-free deodorants/antiperspirants. However, while these compositions address the problems associated with the use of aluminum-based ingredients, they may not always provide optimal odor-reduction and/or absorption.

In the context of anhydrous products, for example sticks and roll-ons, most of the products in the market use starch as an additive, occasionally in combination with sodium bicarbonate. Starch can provide a certain viscosity at high temperatures during the production of the cosmetic products but may not work so well as an odour absorber.

There is therefore a need to provide deodorant cosmetic agents other than the commonly used aluminum and/or zirconium compounds or at least to significantly reduce the amount of these compounds. The deodorant active ingredients should have a good deodorant effect, be well tolerated by the skin and be easy to formulate. In addition, these deodorant/agents should have no negative influence on the storage stability of the cosmetic products used to inhibit body odor.

BRIEF SUMMARY

The objective of the present disclosure is to provide a deodorant composition which has a good skin feeling, good compatibility with the skin, causes minimal textile soiling and has high storage stability. It is a further objective to provide such a composition that is easy to formulate.

Surprisingly, it has been found that the combination of calcium silicate and sodium bicarbonate in a deodorant composition (preferably in an anhydrous deodorant composition) is beneficial in terms of moisture absorption. Additional surprising benefits are disclosed herein.

According to the present disclosure, there is provided a deodorant cosmetic composition comprising calcium silicate and sodium bicarbonate. As is well understood by the skilled person, sodium bicarbonate (which is the INCI name) is also referred to as sodium hydrogen carbonate and as baking soda. Cosmetic products incorporating the cosmetic composition and methods of using the same are also provided.

The deodorant cosmetic composition includes calcium silicate and sodium bicarbonate may further include at least one emollient, at least one structurant, at least one emulsifier and/or at least one water-absorbing component. In addition, the composition may further include at least one deodorant active ingredient. A particularly preferred aspect of the present disclosure is the combined use of calcium silicate and sodium bicarbonate in an anhydrous composition.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In the context of the present disclosure, the term "anhydrous cosmetic compositions" is understood to mean compositions which contain added free water in a total quantity of from about 0 wt. % to about 1.0 wt %, preferably from about 0 to about 0.8 wt. %, more preferably from about 0 wt. % to about 0.5 wt. %, particularly from about 0 to about 0.2 wt. %, relative to the total weight of the cosmetic composition in each case. Free water within the meaning of the present disclosure is understood to mean water that is different from crystalline water, hydration water, similarly molecularly bound water or water bound or absorbed on/by the components that are used.

Furthermore, the term "deodorant active ingredient" in the context of the present disclosure is understood to mean a compound which has antimicrobial and/or enzyme-inhibiting properties. This also includes compounds which can conceal the unpleasant body odor arising from the decomposition of sweat or can positively change the odor perception of body odor. Preference is given to deodorant active ingredients that are not antiperspirant aluminum and/or aluminum zirconium salts. Therefore, preferred anhydrous cosmetic agents of the present disclosure contain about 0 wt. % water soluble antiperspirant aluminum and/or aluminum-zirconium salts, particularly those listed below. It may be possible that limited amounts of Aluminum are introduced by non-soluble Minerals e.g. Silicates or Oxides, relative to the total weight of the cosmetic composition.

The term "odor-absorbing component" in the context of the present disclosure is understood to mean a component which can reversibly and/or irreversibly, preferably irreversibly, absorb liquid and/or gaseous and/or solid compounds.

The specification of "wt. %" herein relates to the weight of a component relative to the total weight of the anhydrous cosmetic composition, unless something different is indicated.

As noted above, it has surprisingly been found that the combination of calcium silicate and sodium bicarbonate in a deodorant composition is beneficial in terms of body odor absorption.

Further, the combination aids the formulation of the compositions, particularly anhydrous compositions, such as anhydrous waxy-based sticks, creams and roll-ons. In such waxy-based formulations, prior to solidification, the composition is in a hot temperature status and may be too liquid to avoid sedimentation of additives. It has surprisingly been found that the presence of calcium silicate increases the viscosity of the hot liquid composition before solidification which means the sedimentation of any powder in the hot liquid is lowered. It is particularly beneficial for the calcium silicate to be in particulate form, and for the particle size to be small. In the context of the present disclosure, a "small" particle size means the D50 value for the particles of the calcium silicate is <100 μm. These unexpected benefits give rise to a composition that is easy to formulate. The beneficial body odor absorption properties also make the compositions suitable for aluminum-salt-free applications. Thus, the present disclosure relates to cosmetic compositions comprising calcium silicate and sodium bicarbonate that are suitable for use as deodorants.

Yet further, the compositions disclosed herein are particularly suitable for anhydrous formulations. If water is present, there is a risk that the baking soda will decompose within the formulation. Thus, preferably, the deodorant compositions disclosed herein are anhydrous deodorant compositions comprising calcium silicate and baking soda.

In the context of the present disclosure, the particulate nature of the calcium silicate refers to the particles of the calcium silicate having a median particle size (D50) ranging from about 0.5 to about 100 microns, preferably from about 0.5 to about 50 microns, more preferably from about 1 to about 30 microns, yet more preferably from about 5 to about 25 microns.

The calcium silicate particle size may be measured by X-ray absorption. A suitable technique is Sedigraph X-ray absorption, using instruments from Micromeritics or by Laser diffraction e.g. using the equipment of Malvern. Such techniques and instruments are well understood by the skilled person.

The calcium silicate may also have a bulk density ranging from about 50 kg/m$^3$ to about 200 kg/m$^3$, preferably from about 75 kg/m$^3$ to about 180 kg/m$^3$. The bulk density is measured in accordance with standard techniques known by the skilled person.

The calcium silicate suitably has a BET surface area particle size ranging from about 80 m$^2$/g to about 400 m$^2$/g. The calcium silicate suitably has a BET surface area particle size ranging from about 100 m$^2$/g to about 350 m$^2$/g, preferably from about 200 m$^2$/g to about 300 m$^2$/g. The surface area particle size may be measured by BET, using instruments from Micromeritics. Such techniques and instruments are well understood by the skilled person.

Suitable commercial products include Zeofree® 250 and Zeofree® 600, both available from Evonik. Zeofree® 250 has a D50 value of around 15 microns, as measured by Sedigraph, and a bulk density of around 150 kg/m$^3$. Zeofree® 600 has a D50 value of around 8 microns, as measured by Sedigraph, a bulk density of around 96 kg/m$^3$ and a BET surface area of around 250 m$^2$/g.

Preferably, the calcium silicate has had no surface modification.

The baking soda may advantageously be in powder form. The powder particles preferably have a particle size ranging from about 1 to about 150 microns, preferably from about 5-100 microns. More preferably, the powder baking soda has a median particle size (D50) of less than 50 μm and wherein about 100 wt. % of the powder baking soda particles have a particle size of less than about 200 μm. The wt. % specification is relative to the total weight of the odor-absorbing component. The median particle size D50 can, for example, be determined by employing dynamic light scattering (DLS) or Laser diffraction or using a Sedigraph method. A suitable commercial product is Bicar CODEX 0/6P available from Solvay.

A yet further advantage of the combination of calcium silicate and baking soda is in relation to the method for manufacturing the compositions. Non-aerosol products such as sticks and creams require the formation of a hot matrix of the ingredients. Without wishing to be bound by theory, it is believed that small particles avoid sedimentation of the ingredients in the hot liquid. Further, a certain viscosity is needed in the hot matrix to avoid phase separation. The inventors have surprisingly found that a combination of calcium silicate and baking soda provides an advantageous viscosity level within the hot liquid. The experimental details are described below. In particular, the inventors observed by visual perception and by shaking, that the viscosity starts to increase at addition of about 0.5 wt % calcium silicate.

It will be appreciated that the present disclosure provides an alternative to the conventional use of starch; the present disclosure is advantageous in terms of achieving certain viscosities at high temperatures during the production of the cosmetic products, as well as providing beneficial and improved odor absorption.

Thus, a preferred aspect of the present disclosure is an anhydrous deodorant cosmetic composition comprising calcium silicate and baking soda.

A yet further advantage of the present disclosure is that the compositions may be formulated with a high proportion of natural products. For example, the compositions may be aluminum-free, as well as silicone free. In addition, the compositions may be formulated with natural based products such as essential oils (for deodorizing and/or fragrance activity), natural oils (e.g., for emollient activity) and natural waxes (e.g., for structurant activity).

Thus, a further preferred aspect of the present disclosure is an anhydrous deodorant cosmetic composition comprising calcium silicate and baking soda, and which is aluminum-free and silicone-free. More preferably, the composition includes natural based ingredients in amounts greater than about 90 wt %, relative to the total weight of the composition. Suitably, the amount of natural based ingredients ranges from about 0.01 wt % to about 80 wt %, for example from about 5 wt % to about 60 wt %, relative to the total weight of the composition.

The amount of the baking soda ranges from about 3 to about 25 wt %, relative to the total weight of the cosmetic composition; preferably from about 5 to about 20 wt %; more preferably from about 8 to about 18 wt %; most preferably from about 10 to about 15 wt %.

The amount of the calcium silicate ranges from about 0.1 to about 20 wt %, relative to the total weight of the cosmetic composition; preferably from about 0.5 to about 15 wt %; more preferably from about 1 to about 10 wt %, most preferably from about 1 to about 8 wt %.

The additional components of the compositions disclosed herein will now be described in further detail. It will be understood by the skilled person that any one of the components listed below may be combined with one or more of the other components, unless otherwise stated.

Emollients/Cosmetic Oils

The cosmetic compositions of the present disclosure suitably contain at least one emollient. The total amount of the or each emollient is typically in the range of from about 0.05 to about 97% by weight of the cosmetic composition, suitably from about 5 to about 90%, preferably from about 7 to about 80%, more preferably from about 10 to about 60% by weight of the cosmetic compositions. As contemplated herein, the or each emollient may be a cosmetic oil. The term "cosmetic oil" in the sense of this present disclosure refers to an oil suitable for cosmetic use which is not miscible with water in all quantities. The cosmetic oil used as contemplated herein is separate from both fragrances and essential oils.

The anhydrous cosmetic compositions of the present disclosure preferably contain a cosmetic oil which is liquid at about 20° C. and about 1,013 mbar. The or each cosmetic oil is suitably chosen from the group of (i) volatile cyclic silicone oils, in particular cyclic and linear silicone oils; (ii) volatile non-silicone oils, in particular liquid paraffin oils and isoparaffin oils; (iii) non-volatile silicone oils; (iv) non-volatile non-silicone oils; and (v) mixtures thereof. The term "volatile oil" refers to oils which have a vapour pressure of from about 2.66 Pa to about 40,000 Pa (from about 0.02 to about 300 mm Hg) at about 20° C. and an ambient pressure of about 1,013 hPa, preferably from about 10 to about 12,000 Pa (from about 0.1 to about 90 mm Hg), further preferably from about 13 to about 3,000 Pa (from about 0.1 to about 23 mm Hg), in particular from about 15 to about 500 Pa (from about 0.1 to about 4 mm Hg). In contrast, the term "non-volatile oils" in the sense of the present disclosure means oils which have a vapour pressure of less than about 2.66 Pa (about 0.02 mm Hg) at about 20° C. and an ambient pressure of about 1,013 hPa.

The volatile and non-volatile silicone oils and volatile and non-volatile non-silicone oils that can be used in the context of the present disclosure are disclosed, for example, in the disclosure regulations DE 10 2010 063 250 A1 and DE 10 2012 222 692 A1.

Volatile cosmetic oils are usually selected from linear silicone oils with the INCI designation dimethicone, and cyclic silicone oils with the INCI designation cyclomethicone. Cyclotrisiloxane (hexamethylcyclotrisiloxane), cyclotetrasiloxane (octamethylcyclotetrasiloxane), cyclopentasiloxane (decamethylcyclopentasiloxane) and cyclohexasiloxane (dodecamethylcyclohexasiloxane) in particular are understood by the INCI term cyclomethicones. These oils have a vapour pressure of approx. 13-15 Pa at about 20° C. Cyclomethicones are state of the art oils well suited for cosmetic compositions, especially for deodorants.

Due to their persistence in the environment, however, it may be suitable to dispense with the use of cyclomethicones. In a specially preferred form of construction, the compositions used in accordance with the present disclosure and the present disclosure contain 0 to less than about 1% by weight, preferably a maximum of about 0.1% by weight, of cyclomethicones, based on the weight of the composition, whereby any blowing agent present is not taken into account.

Preferred compositions contain at least one volatile non-silicone oil due to the drier skin feeling and the faster release of the active ingredient. Preferred volatile non-silicone oils are selected from C9-12 Alkane, C8-C15 Alkane, C8-C16 isoparaffins, in particular isononane, isodecane, isoundecane, isododecane, isotridecane, istetradecane, isopentadecane and isohexadecane, and mixtures thereof. The most preferred components are C9-12 Alkane, Dodecane and/or isodododecane.

It is also possible to formulate inventive products with a low proportion of volatile oils, based on the total weight of the medium or even without volatile oils. Oils particularly favoured by the present disclosure are esters of linear or branched saturated or unsaturated fatty alcohols with 2-30 carbon atoms with linear or branched saturated or unsaturated fatty acids with 2-30 carbon atoms, which may be hydroxylated. It should be noted here that some esters of linear or branched C1-C22 alkanols or C14-C22 alkenols, and some triesters of glycerol are solid under normal conditions with linear or branched C2-C22 carboxylic acids, which may be saturated or unsaturated, such as cetylstearate or glycerol tristearate (=stearin). According to their present disclosure, these esters, which solid under normal conditions, do not constitute cosmetic oils, since they do not meet the condition "liquid under normal conditions". The classification of whether such an ester is liquid or solid under normal conditions is within the general knowledge of the expert. Preferred are esters of linear or branched saturated fatty alcohols with 2-18 carbon atoms with linear or branched saturated or unsaturated fatty acids with 3-18 carbon atoms, which may be hydroxylated. Preferred examples are isopropyl palmitate, isopropyl stearate, isopropyl myristate, 2-hexyl decyl stearate, 2-hexyl decyl laurate, isodecyl neopentanoate, isononylisononanoate, 2-ethyl hexyl palmitate and 2-ethyl hexyl stearate. Also preferred are isopropyl isostearate, isopropyl oleate, isooctyl stearate, isonyl stearate, isocetvlstearate, isononylisononanoate, isotridecvlisononanoate, cetearylisononanoate, 2-ethylhexyllaurate, 2-ethylhexyl isostearate, 2-ethylhexyl cocoate, 2-octyl dodecyl palmitate, butyl octanoic acid 2-butyl octanoate, diisotridecyl acetate, n-butyl stearate, n-hexyllaurate, n-decyloleate, oleyloleate, oleylerucate, erucyloleate, erucylerucate, ethylene glycoldioleate, ethylene glycoldipalmitate, n-hexyllaurate, n-decyloleate, oleyloleate, oleylerucate, erucyloleate, C12-C15 alkyl lactate and di-C12-C13 alkyl malate, and the benzoic esters of linear or branched C8-22 alkanols. Particularly preferred are benzoic acid C12-C15-alkyl esters, e.g. available as commercial product Finsolv TN. Other oil components preferred according to present disclosure are selected from the C8-C22 fatty alcohol esters of monohydric or polyvalent C2-C7 hydroxycarboxylic acids, in particular the esters of glycolic acid, lactic acid, malic acid, tartaric acid, citric acid and salicylic acid. Such esters based on linear C14/15 alkanols, e.g. C12-C15 alkyl lactate and C12/13 alkanols branched in position 2 are available under the trade name Cosmacol® from Nordmann, Rassmann GmbH & Co, Hamburg, in particular the commercial products Cosmacol®, ESI, Cosmacol® EMI and Cosmacol® ETI, Finsolv® TN (C12-C15 alkyl benzoate), as well as benzoic acid esters, e.g. B. available as Finsolv® SB, 2-ethylhexylbenzoate, e.g. available as Finsolv® EB, and benzoic acid-2-octyldodecyl ester, e.g. available as Finsolv® BOD. Another ester oil is triethyl citrate.

The cosmetic compositions may also contain an ester of a C3-C30-carboxylic acid, preferably an ester from the group ethylhexyl palmitate, isopropyl palmitate and triethyl citrate.

Other oils may contain branched saturated or unsaturated fatty alcohols with 6-30 carbon atoms. These alcohols are often referred to as Guerbet alcohols because they are available after the Guerbet reaction. Preferred alcohol oils are 2-hexyldecanol, 2-octyldodecanol and 2-ethylhexyl alcohol. Isostearyl alcohol is also preferred. Other preferred non-volatile oils are selected from mixtures of Guerbet alcohols and Guerbet alcohol esters, e.g. 2-hexyldecanol and 2-hexyldecyllaurate. The term "triglyceride" used below means "glycerol triester".

Other emollients are selected from the triglycerides of linear or branched, saturated or unsaturated, optionally hydroxylated C8-30 fatty acids, provided that these are liquid under normal conditions. Natural ingredients are particularly preferred, and may be selected from soybean oil, cottonseed oil, sunflower oil, palm oil, palm kernel oil, coconut oil, linseed oil, almond oil, castor oil, corn oil, rapeseed oil, olive oil, sesame oil, safflower oil, wheat germ oil, peach seed oil. Just the liquid components of coconut oil and the like can also be particularly suitable. Particularly preferred are synthetic triglyceride oils, especially Capric/Caprylic triglycerides, e.g. the commercial products Myritol® 318 or Myritol® 331 (BASF/Cognis) with unbranched fatty acid residues and glyceryl triisostearin and glyceryl tri(2-ethyl hexanoate) with branched fatty acid residues. Other suitable ingredients include those with the INCI designations Coco-Caprylate and Coco-Caprylate/Caprate.

Other non-volatile non-silicone oils particularly favoured are selected from the dicarboxylic acid esters of linear or branched. C2-C10 alkanols, in particular diisopropyl adipate, adipate, di-(2-ethylhexyl)adipate, dioctyl adipate, diethyl-/Di-n-butyl/Dioctylsebacate, diisopropylsebacate, dioctylmalate, dioctyl maleate, dicaprylylm maleate, diisooctylsuccinate, di-2-ethylhexyl succinate and di-(2-hexyldecyl)-succinate.

Other non-volatile non-silicone oils which are particularly preferred according to present disclosure are selected from the addition products of from about 1 to about 5 propylene oxide units to monovalent or polyvalent C8-22 alkanols such as octanol, decanol, decanediol, lauryl alcohol, myristyl alcohol and stearyl alcohol, e.g. PPG-2 myristyle ether and PPG-3 myristyle ether.

Other non-volatile non-silicone oils particularly preferred as contemplated herein are selected from the addition products of at least about 6 ethylene oxide and/or propylene oxide units to monovalent or polyvalent C3-22 alkanols such as glycerol, butanol, butanediol, myristyl alcohol and stearyl alcohol, which may esterify if desired, e.g. PPG-14-butyl ether, PPG-9-butyl ether, PPG-10-butanediol and PPG-15-stearyl ether.

Other non-volatile non-silicone oils which are particularly preferred as contemplated herein are selected from the symmetrical, asymmetrical or cyclic esters of carbonic acid with C6-C20 alcohols, e.g. di-n-caprylyl carbonate (CetioIlk CC) or di-(2-ethylhexyl)carbonate (Tegosoft DEC). Esters of carbonic acid with C1-05 alcohols, e.g. glycerol carbonate or propylene carbonate, are not suitable as cosmetic oil compounds.

Other oils which may be preferred by present disclosure are selected from the esters of dimers of unsaturated C12-C22 fatty acids (dimer fatty acids) with monovalent linear, branched or cyclic C2-C18 alkanols or with polyvalent linear or branched C2-C6 alkanols. Especially preferably, the total weight of dimer fatty acid esters is from about 0.1-10% by weight, preferably from about 1-5% by weight, in each case based on the entire composition, without taking into account any blowing agent present.

Lower melting point lipid or wax components may be used as the emollient. Such products allow consistent optimization of stick or cream products and minimization of visible residues on the skin. Particularly preferred are products with the INCI designation Cocoglycerides, and products with the INCI designation Hydrogenated Cocoglycerides. Optionally, use may be made of Myristyl Myristate, the pasty fraction or a mix of the liquid and pasty fraction of Coconut Oil, and/or Shea Butter. One or more of these ingredients, can be beneficial to achieve the right consistency of the cosmetic product.

The total amount of the or each emollient is preferably in the range of from about 2.0 to about 85% by weight of the cosmetic composition, preferably from about 10 to about 75% by weight, further preferably from about 20 to about 70% by weight, still further preferably from about 30 to about 65% by weight.

Structurants/Waxes

The term "waxes" in this present disclosure refers to substances which can be kneaded at about 20° C. or are hard to brittle, have a coarse to fine crystalline structure and are translucent to opaque in colour, but not vitreous. Furthermore, these substances melt above about 30° C. without decomposition, are slightly liquid (little viscous) just above the melting point, have a strongly temperature-dependent consistency and solubility and can be polished under slight pressure.

The term "fatty acids", as used in this present disclosure, refers to aliphatic carboxylic acids containing unbranched or branched carbon radicals with 4 to 40 carbon atoms. The fatty acids used in this present disclosure can be both naturally occurring and synthetically produced fatty acids. Furthermore, the fatty acids can be monounsaturated or polyunsaturated and may also contain Hydroxyl groups in the sidechain.

The term "fatty alcohols" in this present disclosure refers to aliphatic, monovalent, primary alcohols containing unbranched or branched hydrocarbon radicals with 4 to 40 carbon atoms. The fatty alcohols used in the present disclosure may also be mono- or polyunsaturated.

The anhydrous deodorizing cosmetic compositions as contemplated herein may contain at least one structurant. The total amount of the or each structurant is typically in the range of from about 0.05 to about 97% by weight of the cosmetic composition, suitably from about 5 to about 90%, preferably from about 10 to about 80%, more preferably from about 20 to about 60% by weight of the cosmetic compositions. Suitable structurants are waxes selected from the group of (i) fatty acid glycerol mono-, di- and triesters; (ii) Butyrospermum Parkii (Shea butter); (iii) esters of saturated monohydric C8-18 alcohols with saturated C12-18 monocarboxylic acids; (iv) linear primary C12-C24 alkanols; (v) esters of a saturated monovalent C16-60 alkanol and a saturated C8-C36 monocarboxylic acid; (vi) glycerol triesters of saturated linear C12-30 carboxylic acids which may be hydroxylated, such as glycerol esters of hydrogenated vegetable oils; (vii) natural vegetable waxes; (viii) animal waxes; (ix) synthetic waxes; and (x) mixtures thereof.

In the context of the present disclosure preferably usable waxes are disclosed in the document DE 10 2012 222 692 A1.

Natural vegetable waxes may be used, such as candelilla wax, carnauba wax, Japan wax, sugar cane wax, ouricoury wax, cork wax, and sunflower wax. Fruit waxes may also be used, such as orange wax, lemon wax and grapefruit wax. Animal waxes may also be used such as beeswax, shellac wax and spermaceti. It is also possible to use hydrogenated or hardened waxes. Chemically modified waxes, especially hard waxes such as montan ester waxes, hydrogenated jojoba waxes and Sasol waxes, can also be used as wax components. Synthetic waxes include polyalkylene waxes and polyethylene glycol waxes, C20-C40 dialkyl esters of dimer acids, C30-50 alkyl beeswax and alkyl and alkylaryl esters of dimer fatty acids.

Other preferred lipid or wax components with a melting point >50° C. are the triglycerides of saturated and optionally hydroxylated C12-30 fatty acids, such as hydrogenated triglyceride fats (hydrogenated palm oil, hydrogenated coconut oil, hydrogenated castor oil and hydrogenated rapeseed oil), glyceryl tribehenate (tribehenin) or glyceryl tri-12-hydroxystearate, furthermore synthetic full esters of fatty acids and glycols or polyols with 2-6 carbon atoms as long as they have a melting point above about 50° C., e.g. preferably C18-C36 acid triglycerides. As contemplated herein, hydrogenated castor oil, available e.g. as Cutina® HR, is particularly preferred as a wax component.

Other preferred lipid or wax components with a melting point >50° C. are the saturated linear C14-C36 carboxylic acids, especially myristic acid, palmitic acid, stearic acid and behenic acid as well as mixtures of these compounds. Esters of saturated monohydric C12-C18 alcohols with saturated. C12-C18 monocarboxylic acids may also be used, such as stearyl laurate, cetearyl stearate, and cetyl palmitate.

Preferred linear primary C12-C24 alkanols include Cetyl Alcohol, Stearyl Alcohol and mixtures thereof.

The total amount of the or each structurant preferably ranges from about 1.0 to about 60% by weight, preferably from about 2.0 to about 40% by weight, preferably from about 5.0 to about 35% by weight, especially from about 6.0 to about 30% by weight, based on the total weight of the deodorizing cosmetic agent.

Water-Absorbing Compounds

The anhydrous cosmetic compositions as contemplated herein may contain at least one water-absorbing component. The at least one water-absorbing component is suitably selected from the group of celluloses, microcrystalline celluloses, modified celluloses, maltodextrin, starch and their derivatives, silica, modified silica, Talc, kaolin, bentons, hectorites, silicas, pearlites, metal oxides, metal hydroxides, metal carbonates, metal silicates (other than calcium silicate), metal oxide hydroxides, metal oxide carbonates, metal hydroxide carbonates, metal hydrogen carbonates (other than baking soda), isolated plant components and mixtures thereof, in particular of hydrophilic silica and/or cellulose. Preferred water-absorbing components include starches. Suitable starches may be selected from Zea Mays (Corn) Starch, Arrow Root Starch, Tapioca starch, Rice Starch, and Potato Starch.

Furthermore, starch derivatives in the context of this present disclosure are starch compounds which have been modified using chemical reactions.

Modified silica can be obtained, for example, by surface modification using various chemical compounds.

The isolated plant components mentioned above can also be ground and used in powder form. A preferred plant component is Bambusa Arundiacea Stem Extract.

The water-absorbent components also include hydrophilic silica with a BET surface area of from about 250 to about 350 $m^2/g$ (commercially available under the trade name Aeropearl® 300/30 from Evonik) and/or cellulose (commercially available under the name Sensocel OC 30 G from CFF, for example).

As contemplated herein, it has been found that use of water-absorbing compounds in powder form with a certain median particle size is also advantageous. Therefore, preferred a water-absorbing component are present in particle form, wherein at least about 30 wt. % of the water-absorbing component has a median particle size D50 of more than about 10 µm and wherein about 100 wt. % of the water-absorbing component has a median particle size D50 of less than about 200 µm. The wt. % specification is relative to the total weight of the water-absorbing component. The median particle size D50 can, for example, be determined by employing dynamic light scattering (DLS) or using a Sedigraph method.

The water-absorbing ingredient may be a starch, more preferably a starch having a particle size with a D50 value ranging from about 1 to about 100 microns; more preferably from about 5 to about 50 microns. The total amount of the at least one water-absorbing component (preferably, the component is a starch) ranges from 0 to about 30 wt %, suitably from about 2.0 to about 25% by weight, preferably from about 3.0 to about 20% by weight, especially from about 4.0 to about 15% by weight, relative to the total weight of the cosmetic composition.

Emulsifer

The anhydrous cosmetic compositions as contemplated herein may contain at least one emulsifier. As contemplated herein, suitable emulsifiers and surfactants are preferably selected from anionic, cationic, non-ionic, amphoteric, particularly ampholytic and zwitterionic emulsifiers and surfactants. Surfactants are amphiphilic (bifunctional) compounds that include at least one hydrophobe and at least one hydrophile molecular part. The hydrophobic radical is preferably a hydrocarbon chain with from about 8 to about 28 carbon atoms, which can be saturated or unsaturated, linear or branched. It is especially preferable if this C8-C28 alkyl chain is linear.

Anionic surfactants are understood to mean surfactants having exclusively anionic charges; they contain, for example, carboxyl groups, sulfonic acid groups or sulfate groups. Particularly preferred anionic surfactants are alkyl sulfates, alkyl ether sulfates, acylglutamates and C8-24-carboxylic acids and salts thereof, so-called soaps.

Cationic surfactants are understood to mean surfactants having exclusively cationic charges; they contain, for example, quaternary ammonium groups. Preference is given to cationic surfactants of the type of quaternary ammonium compounds, esterquats and amidoamines. Preferred quaternary ammonium compounds are ammonium halides and the imidazolium compounds known under the INCI designations quaternium-27 and quaternium-83. As contemplated herein, the quaternized protein hydrolysates can also be used. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines.

The amphoteric surfactants are divided into ampholytic surfactants and zwitterionic surfactants. Ampholytic surfactants are surface active compounds that contain both acid (for example, —COOH or —SO$_3$H groups) and also alkaline hydrophilic groups (for example, amino groups) and have acidic or alkaline behavior depending on the condition. Zwitterionic surfactants are specialist surfactants that carry both a negative and a positive charge in the same molecule. Examples of preferred zwitterionic surfactants are betaines, the N-alkyl-N,N-dimethylammoniumglycinates, N-acylaminopropyl-N,N-dimethylammoniumglycinate and the 2-alkyl-3-carboxymethyl-3-hydroxyethyl-imidazolines, each having from about 8 to about 24 carbon atoms in the alkyl group. Examples of preferred ampholytic surfactants are N-alkylglycines, N-alkylaminopropionic acids, N-alkylaminobutyric acids, N-alkyliminodipropionic acids, N-hydroxyethyl-n-alkylamidopropyl-glycines, N-alkyl taurines, N-alkyl sarcosines, 2-alkylaminopropionic acids and alkylaminoacetic acids having from about 8 to about 24 carbon atoms in the alkyl group in each case.

Examples of preferred nonionic surfactants which have no charged or ionizable groups are (i) linear saturated alcohols having from about 12 to about 30 carbon atoms, (ii) esters and partial esters of a polyol having from about 3 to about 6 carbon atoms and linear saturated and unsaturated fatty acids having from about 12 to about 30 carbon atoms, which can be hydroxylated, (iii) sterols and ethoxylated sterols, (iv) alkanols and carboxylic acids having in each case from about 8 to about 24 carbon atoms and on average from about 1 to about 100 ethylene oxide units per molecule, (v) glycerol monoethers of saturated and/or unsaturated, branched and/or unbranched alcohols having a chain length of from about 8 to about 30 carbon atoms, (vi) partial esters of polyglycerols having from about 2 to about 10 glycerol units, which are saturated or unsaturated with from about 1 to about 5 saturated or unsaturated, linear or branched carboxylic acids having from about 8 to about 30 carbon atoms, which can be hydroxylated, (vii) silicone copolyols with ethylene oxide units or with ethylene oxide and propylene oxide units, (viii) alkyl mono- and oligoglycosides having from about 8 to about 22 carbon atoms in the alkyl radical and their ethoxylated analogs and (ix) mixtures thereof.

In the context of the present disclosure, emulsifiers and surfactants that can preferably be used are, for example, disclosed in the German patent applications with the numbers DE 10 2012 222 692 A1, DE 10 2010 063 250 A1 and DE 10 2010 055 816 A1.

Preferred cosmetic compositions contain a nonionic emulsifier from the group of polyalkylene glycol ethers, preferably from the group of alkoxylated C8-C24 alkanols with an average of from about 10-100 moles of alkylene oxide per mole, preferably from the group of ethoxylated C12-C18 alkanols with an average of from about 10-30 moles of ethylene oxide per mole.

The ethoxylated C8-C24 carboxylic acids have the formula R1(OCH$_2$CH$_2$)$_n$OH, where R1 is a linear or branched saturated or unsaturated acyl radical having 8-24 carbon atoms and n, the average number of ethylene oxide units per molecule, is from about 10-100, preferably from about 10-30 mol of ethylene oxide per 1 mol of caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachic acid, gadoleic acid, behenic acid, erucic acid and brassidic acid and their technical mixtures. Particularly preferred C8-C22 alkyl mono- and oligoglycosides are selected from octyl glucoside, decyl glucoside, lauryl glucoside, palmityl glucoside, cetearyl glucoside, isostearyl glucoside, stearyl glucoside, arachidyl glucoside and behenyl glucoside and mixtures thereof. It is also possible to use a mixture of an ethoxylated C8-C24 carboxylic acid with a fatty acid, for example with cetearyl alcohol or stearyl alcohol. Particularly preferred is a mixture of cetearyl alcohol and cetearyl glucoside.

Particularly preferred compositions emulsifier is contained in a total amount of from about 0.1-10% by weight, especially preferably from about 0.5-6% by weight and extraordinarily preferably from about 0.7-4% by weight, based on the total composition.

Deodorant Active

The deodorant effect of the anhydrous cosmetic compositions of the present disclosure can be further increased if at least one deodorant active substance with antibacterial and/or bacteriostatic and/or enzyme-inhibiting and/or odor-neutralising and/or odor-absorbing effect is present. Suitably, such agent(s) are present in a total amount of from about 0.0001 to about 40% by weight preferably from about 0.2 to about 20% by weight, preferably from about 1 to about 15% by weight, in particular from about 1.5 to about 5.0% by weight, based on the total weight of the deodorant cosmetic composition.

If ethanol is used in the means used as contemplated herein, it is not considered to be a deodorant active substance in the context of the present disclosure, but as a component of the carrier. Suitable deodorant active ingredients, for example, are disclosed in the disclosure document DE 10 2010 063 250 A1.

The anhydrous cosmetic composition may contain at least one deodorant active ingredient. This deodorant active ingredient differs from the calcium silicate and the baking soda previously described. The at least one deodorant active ingredient may be selected from the group of (i) arylsulfatase inhibitors, beta-glucuronidase inhibitors, aminoacylase inhibitors, esterase inhibitors, lipase inhibitors and lipoxygenase inhibitors; (ii) α-monoalkyl glycerol ethers having a branched or linear saturated or unsaturated, optionally hydroxylated C6-C22-alkyl radical, in particular α-(2-ethylhexyl) glycerol ethers, (iii) alcohols, in particular phenoxyethanol, benzyl heptanol, 1,2-hexanediol, 1,2-octanediol, 1,2-decanediol, tropolone and butyloctanoic acid; (iv) germ-inhibiting perfume oils, which may be composed out of IFRA-conform perfume ingredients providing a minimum bacteriostatic effect; (v) essential oils, such as Rosmarinus Officinalis (Rosemary) Oil, Clove oil, Thyme oil, Cinnamon oil, Laurel oil, and any oil from the fruits of the Citrus family, as well as mixtures thereof, (vi) prebiotically active components; (vii) trialkyl citric acid esters, in particular triethyl citrate; (viii) active substances which influence the number of skin germs from the group of staphylococci involved in the odor formation, coryneform bacteria, anaerococci and micrococci or inhibit their growth; (ix) zinc and silver compounds, in particular zinc phenolsulfonate, bischloride(−1)-octahydroxy-pentazinc, zinc citrate and silver lactate; (x) organohalogen compounds, in particular triclosan, chlorhexidine and chlorhexidine gluconate; (xi) benzalkonium halides, in particular benzalkonium chloride and benzethonium chloride; (xii) quaternary ammonium compounds, in particular cetylpyridinium chloride; (xii) antimicrobially active carbonates, phosphates and sulfates, in particular cocamidopropyl PG-dimonium chloride phosphate, disodium pyrophosphate and soya morpholinium ethosulfate; (xiii) Lantibiotics; (xiv) aluminum and aluminum zirconium salts; (xv) bispyridines, in particular octenidine; (xvi) antimicrobially active acids, in particular caprylic hydroxamic acid, carnesol acid and tartaric acid; (xvii) polyglycerol esters; (xviii) sorbitan esters and lactones, in particular sorbitan caprylate and glucono-1,5-lactone; (xix) and mixtures thereof, in particular phenoxyethanol and/or caprylyl glycol and/or 1,2-hexanediol and/or α-(2-ethylhexyl) glycerol ether.

Furthermore, sodium phenol sulfonate as well as e.g. the components of lime blossom oil can be used. Weaker antimicrobial substances that have a specific effect against the gram-positive germs responsible for sweat breakdown can also be used as deodorant active substances. Benzyl alcohol can also be used as a deodorant agent. Other antibacterial deodorants are lantibiotics, glycoglycerolipids, sphingolipids (ceramides), sterols and other active ingredients that inhibit bacterial adhesion to the skin, e.g. glycosidases, lipases, proteases, carbohydrates, di- and oligosaccharide fatty acid esters and alkylated mono- and oligosaccharides. Preferred deodorant active ingredients are long-chain diols, e.g. 1,2-alkane-(C5-C18)diols, glycerol mono(C8-C18)-fatty acid esters or, especially preferably, glycerol mono-(C6-C16)-alkyl ethers, especially 2-ethylhexylglycerol ethers, which are very well tolerated by the skin and mucous membranes and are effective against corynebacteria, as well as phenoxyethanol, phenoxyisopropanol (3-phenoxy-propan-2-ol), anis alcohol, 2-methyl-5-phenyl-pentan-1-ol, 1,1-dimethyl-3-phenyl-propan-1-ol, benzyl alcohol, 2-phenylethan-1-ol, 3-phenylpropan-1-ol, 4-phenylbutan-1-ol, 5-phenylpentan-1-ol, 2-benzylheptan-1-ol, 2,2-dimethyl-3-phenylpropan-1-ol, 2,2 Dimethyl-3-(3'-methylphenyl)-propan-1-ol, 2-ethyl-3-phenylpropan-1-ol, 2-ethyl-3-(3'-methylphenyl)-propan-1-ol, 3-(3'-chlorophenyl)-2-ethylpropan-1-ol, 3-(2'-chlorophenyl)-2-ethylpropan-1-ol, 3 (4'-chlorophenyl)-2-ethylpropan-1-ol, 3-(3%4'-dichlorophenyl)-2-ethylpropan-1-ol, 2Ethyl-3-(2'-methylphenyl)-propan-1-ol, 2-ethyl-3-(4'-methylphenyl)-propan-1-ol, 3-(3',4'-dimethylphenyl)-2-ethylpropan-1-ol, 2-Ethyl-3-(4'-methoxyphenyl)-propan-1-ol, 3-(3',4'-dimethoxyphenyl)-2-ethylpropan-1-ol, 2-allyl-3-phenylpropan-1-ol and 2-n-pentyl-3-phenylpropan-1-ol.

A preferred odor-absorbing ingredient is calcium carbonate, more preferably precipitated calcium carbonate. The precipitated calcium carbonate may be present in particulate form, wherein the particles have a median particle size (D50) ranging from about 0.5 to about 40 microns, preferably from about 1 to about 20 microns more preferably from about 1 to about 15 microns (particle size measurement techniques are the same as those provided above in relation to the calcium silicate). The particles suitably have a median particle size (D50) ranging from about 1 to about 10 microns; preferably from about 1 to about 5 microns; more preferably from about 2 to about 4 microns. The calcium carbonate preferably has an apparent density after tamping ranging from about 0.5 kg/dm$^3$ to about 1.0 kg/dm$^3$; the calcium carbonate may have an apparent density after tamping ranging from about 0.6 kg/dm$^3$ to about 0.9 kg/dm$^3$, preferably from about 0.6 kg/dm$^3$ to about 0.8 kg/dm$^3$, more preferably around 0.7 kg/dm$^3$. Apparent density is measured in accordance with DIN EN ISO 787-11. This technique is well understood by the skilled person. The calcium carbonate preferably has a BET surface area particle size ranging from about 2 m$^2$/g to about 8 m$^2$/g; the calcium carbonate may have a BET surface area ranging from about 3 m$^2$/g to about 6 m$^2$/g, preferably from about 4 m$^2$/g to about 7 m$^2$/g, more preferably from about 4 m$^2$/g to about 6 m$^2$/g, suitably around 5 m$^2$/g. A suitable commercial product is PRECAfood® available from Schafer Kalk. This product has a D50 value of around 3 microns, as measured by Sedigraph, a tamped density of around 0.7 kg/dm$^3$, and a BET specific surface area of around 5 m$^2$/g Preferably, the anhydrous deodorant cosmetic compositions disclosed herein are water-soluble aluminum-salt free, so a preferred aspect is exemplified as comprising no deodorant water-soluble aluminum or water-soluble aluminum-zirconium salts and no water-soluble antiperspirant aluminum or aluminum-zirconium salts. The compositions may also be exemplified as ACH-free (i.e. free of Aluminium chlorohydrate).

It is preferable if the at least one deodorant active ingredient, particularly the aforementioned particularly preferred deodorant active ingredients, is used in a specific total amount. In this connection, the term total amount is understood to mean the sum of the quantities of all deodorant active ingredients. Therefore, if a mixture of different deodorant active ingredients is used, the following quantity specifications relate to the total amount of the mixture of deodorant active ingredients. Therefore, preferred embodiments of the present disclosure are exemplified in that the at least one deodorant active ingredient is contained in a total quantity of from about 0.0001 to about 25 wt. %, preferably from about 0.001 to about 20 wt. %, more preferably from about 0.01 to about 15 wt. %, and most preferably from about 0.5 to about 15 wt. %, relative to the total weight of the anhydrous cosmetic composition.

Antiperspirant Actives

The compositions as contemplated herein may comprise at least one antiperspirant agent, i.e. at least one ingredient that has antiperspirant properties.

The term "antiperspirant" is intended to mean the reduction or reduction of perspiration of the body's eccrine sweat glands. The anhydrous deodorant cosmetic compositions of the present disclosure may also have antiperspirant activity, either through the action of the mandatory components, or with the addition of at least one antiperspirant agent.

It will be appreciated from this disclosure that any antiperspirant actives present in the composition of the present disclosure are preferably free of water-soluble salts of aluminium and/or aluminium-zirconium. Thus, cosmetic compositions as contemplated herein preferably contain no deodorizing and no antiperspirant water-soluble salts of aluminium and/or aluminium-zirconium. In particular, none of the following deodorizing and/or antiperspirant salts of aluminium and/or aluminium-zirconium are preferably contained:

(i) water-soluble astringent inorganic salts of aluminium, in particular aluminium chlorohydrate, aluminium sesquichlorohydrate, aluminium dichlorohydrate, aluminium hydroxide, potassium aluminium sulphate, aluminium bromohydrate, aluminium chloride, aluminium sulphate;

(ii) water-soluble astringent organic salts of aluminium, in particular aluminium chlorohydrex-propylene glycol, aluminium chlorohydrex-polyethylene glycol, aluminium propylene glycol complexes, aluminium sesquichlorohydrex-propylene glycol, aluminium sesqui-chlorohydrex-polyethylene glycol, Aluminium propylene glycol dichlorohydrex, aluminium poly-ethylene glycol dichlorohydrex, aluminium undecylenoyl collagen amino acid, sodium aluminium lactate, sodium aluminium chlorohydroxylactate, aluminium lipoamino acids, aluminium lactate, aluminium chlorohydroxyallantoinate, sodium aluminium chlorohydroxylactate;

(iii) water-soluble astringent inorganic aluminium-zirconium salts, in particular aluminium zirconium trichlorohydrate, aluminium zirconium tetrachlorohydrate, aluminium zirconium pentachlorohydrate, aluminium zirconium octachlorohydrate;

(iv) water-soluble astringent organic aluminium-zirconium salts, in particular aluminium-zirconium-propylene glycol complexes, aluminium-irconium trichlohydrexglycine, alumi niumzirconiumtetrachlorohydrexglycine, aluminium zirconium pentachlorohydrexglycine, aluminium zirconium octachlorohydrexglycine; and (v) their mixtures.

Additional Components

Furthermore, the cosmetic composition can contain additional ingredients. These ingredients are preferably selected from the group of (i) fragrances; (ii), chelating agents; (iii) polyethylene glycols; (iv) skin-cooling active ingredients; (v) pH control agents; (vi) skin-care active ingredients, such as moisturizers, skin-calming substances, skin-lightening substances, skin-smoothing substances, UV protection substances, substances promoting skin circulation, substances to improve skin impurities, substances to protect against oxidative substances, substances to protect against free radicals, substances to protect against skin aging, and anti-inflammatory substances; (vii) preservatives; and (viii) mixtures thereof. The compositions can also optionally be dyed with natural or synthetic dyes, which are regulated by national legislation in positive lists, e.g. in the appendix of the Cosmetics Ordinance.

Preferred embodiments of the present disclosure contain at least one fragrance, in addition to the aforementioned components. As contemplated herein, this is understood to mean substances having a molar mass of from about 74 to about 300 g/mol, which contain at least one osmotic group in the molecule and have an odor and/or taste, i.e. they are capable of exciting the receptors of the hair cells of the olfactory system. Osmotic groups are groups bound covalently to the molecular structure in the form of hydroxyl groups, formyl groups, oxo groups, alkoxycarbonyl groups, nitrile groups, nitro groups, azide groups, etc. in this context, the term "fragrances" in the context of the present disclosure also comprises perfume oils which are liquid at about 20° C. and about 1.013 hPa, perfumes, or perfume oil constituents. Fragrances that can be used within the scope of the present disclosure are, for example, (i) esters, in particular benzyl acetate, phenoxyethyl isobutyrate, p-tert.-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmecyclate; (ii) ethers, in particular benzyl ethyl ether and ambroxol; (iii) aldehydes, in particular linear alkanals having from about 8 to about 18 carbon atoms, citral, citronellal, citronellyloxyacetaldehyde, cyclamen aldehyde, lilial and bourgeonal; (iv) ketones, in particular ionones, alpha-isomethylionone and methyl cedryl ketone; (v) alcohols, in particular anethol, citronellol, eugenol, geraniol, linalool, phenylethyl alcohol and terpineol; (vi) hydrocarbons, in particular terpenes such as limonene and pinene; and (vii) mixtures thereof. However, mixtures of different fragrances which produce a pleasant scent together are preferred.

Particularly preferred cosmetic compositions as contemplated herein are obtained if the fragrance is present in a total amount of from about 0.00001 to about 10 wt. %, preferably from about 0.001 to about 9.0 wt. %, more preferably from about 0.01 to about 8.0 wt. %, more preferably from about 0.5 to about 7.0 wt. %, particularly from about 1 to about 6.0 wt. %, relative to the total weight of the anhydrous cosmetic composition.

Particularly preferred examples of the composition as contemplated herein are described below (all specifications in wt. %). All compositions below have a total amount of free water of from about 0 to about 1.0 wt. %, particularly from about 0 to about 0.2 wt. %, relative to the total weight of the respective embodiment.

TABLE 1 cream formulations C1-C5

| Ingredient (INCI name) | C1 | C2 | C3 | C4 | C5 |
|---|---|---|---|---|---|
| Cocos Nucifera (Coconut) Oil | 38.5 | 30 | 38.8 | 39.5 | 32.9 |
| Butyrospermum Parkii (Shea) Butter | 5 | | 5 | | |
| Stearyl Alcohol | 8 | 7 | 8 | 6 | 6 |
| Hydrogenated Castor Oil | 2.5 | 3 | 1.5 | 3 | 2.5 |
| Hydrogenated Rapeseed Oil | | | | 0.5 | |
| Sodium Bicarbonate | 9 | 12 | 15 | 15 | 15 |
| ZEA MAYS (CORN) STARCH | 10 | 12 | | 10 | 8.5 |
| Arrow Root Starch | | | 10 | | 5 |
| Calcium carbonate, PCC | | | | 3 | 5 |
| Coco-Caprylate | | 20 | | | |
| Caprylic/Capric Triglyceride | 25 | 12 | 20 | 10 | |
| C9-12 Alkane | | | | | 20 |
| Coco-Caprylate/Caprate | | | | 10 | |
| Cocoglycerides | | | | | 3 |
| Myristyl Myristate | | 2 | | | |
| Calcium Silicate | 1 | 1 | 0.5 | 2 | 1.5 |
| Parfum | 1 | 1 | 1 | 1 | 0.6 |
| Rosmarinus Officinalis (Rosemary) Oil | | | 0.2 | | |
| TOTAL | 100 | 100 | 100 | 100 | 100 |

TABLE 2 cream formulations C6-C10

| Ingredient (INCI name) | C6 | C7 | C8 | C9 | C10 |
|---|---|---|---|---|---|
| Cocos Nucifera (Coconut) Oil | 34 | 32 | 32 | 29 | 24.5 |
| Butyrospermum Parkii (Shea) Butter | | 5 | 1.5 | 5 | 5.7 |

TABLE 2-continued cream formulations C6-C10

| Ingredient (INCI name) | C6 | C7 | C8 | C9 | C10 |
|---|---|---|---|---|---|
| Stearyl Alcohol | 6 | 6 | 6 | 6 | 6 |
| Hydrogenated Castor Oil | 3 | 2 | 2 | 2 | 2.5 |
| Hydrogenated Rapeseed Oil | | 1 | | | |
| Sodium Bicarbonate | 10 | 15 | 15 | 15 | 10 |
| ZEA MAYS (CORN) STARCH | 10 | | 12 | 10 | 15 |
| Arrow Root Starch | | 15 | | | |
| Calciumcarbonate, PCC | 10 | | 5 | 5 | 5 |
| Coco-Caprylate | | | | | |
| Caprylic/Capric Triglyceride | 20 | | | | 25 |
| Cocoglycerides | | 20 | 10 | 25 | |
| C9-12 Alkane | | | 10 | | |
| Myristyl Myristate | 5 | | 3 | | |
| Calcium Silicate | 1 | 3 | 2.5 | 2 | 5 |
| Cetearyl Alcohol, Cetearyl Glucoside | | | | | 1 |
| Parfum | 1 | 1 | 1 | 1 | |
| Rosmarinus Officinalis (Rosemary) Oil | | | | | 0.3 |
| TOTAL | 100 | 100 | 100 | 100 | 100 |

TABLE 3 stick formulations S1-S5

| Ingredient (INCI name) | S1 | S2 | S3 | S4 | S5 |
|---|---|---|---|---|---|
| Cocos Nucifera (Coconut) Oil | 19.5 | 14.7 | 26.5 | 29.4 | 28 |
| Butyrospermum Parkii (Shea) Butter | 5 | | 5 | | |
| Cetyl Alcohol | | 0.3 | | | |
| Stearyl Alcohol | 18 | 17 | 15 | 17 | 15 |
| Hydrogenated Castor Oil | 1.5 | 3 | 1.2 | 1.5 | 2.5 |
| Hydrogenated Rapeseed Oil | | | | 0.5 | |
| Sodium Bicarbonate | 15 | 13.5 | 15 | 15 | 10 |
| ZEA MAYS (CORN) STARCH | 15 | 12.5 | | 5 | 5 |
| Arrow Root Starch | | | 9 | | 5 |
| Calciumcarbonate, PCC | 0 | 3 | 5 | 10 | 10 |
| Caprylic/Capric Triglyceride | 24 | 12 | 20 | 10 | |
| C9-12 Alkane | | 20 | | | 20 |
| Coco-Caprylate/Caprate | | | | 10 | |
| Cocoglycerides | | | | | 3 |
| Myristyl Myristate | | 2 | | | |
| Calcium Silicate | 1 | 1 | 2 | 1 | 0.5 |
| Parfum | 1 | 1 | 1 | 0.6 | 1 |
| Rosmarinus Officinalis (Rosemary) Oil | | | 0.3 | | |
| TOTAL | 100 | 100 | 100 | 100 | 100 |

TABLE 4 stick formulations S6-S11

| Ingredient (INCI name) | S6 | S7 | S8 | S9 | S10 | S11 |
|---|---|---|---|---|---|---|
| Cocos Nucifera (Coconut) Oil | 26 | 12 | 19 | 15 | 23.5 | 27.3 |
| Butyrospermum Parkii (Shea) Butter | | 5 | 2 | 5 | 5 | 5 |
| Stearyl Alcohol | 20 | 20 | 18 | 20 | 18 | 18 |
| Hydrogenated Castor Oil | 1.5 | 2 | 2 | 2 | 1.5 | 1.5 |
| Sodium Bicarbonate | 10 | 13 | 15 | 15 | 15 | 15 |
| ZEA MAYS (CORN) STARCH | | | 5 | | | |
| Arrow Root Starch | 10 | | | | | |
| Calciumcarbonate, PCC | 10 | 15 | 14 | 15 | 5 | 0 |
| Caprylic/Capric Triglyceride | | | | | 25 | 20 |
| Cocoglycerides | 20 | 30 | 10 | 25 | | 5 |
| C9-12 Alkane | | | | 10 | | |
| Myristyl Myristate | | | 3 | | | |
| Calcium Silicate | 1.5 | 2 | 1 | 2 | 5 | 8 |
| Cetearyl Alcohol, Cetearyl Glucoside | | | | | 1 | |
| Parfum | 1 | 1 | 1 | 1 | 1 | |
| Rosmarinus Officinalis (Rosemary) Oil | | | | | | 0.2 |
| TOTAL | 100 | 100 | 100 | 100 | 100 | 100 |

The formulation of the composition in a specific dosage form, such as a roll-on, a stick or a creme/wax is preferentially based on the requirements of the intended use. Therefore, depending on the intended use, the compositions can be produced in a solid, semi-solid manner, liquid, dispersed, emulsified, suspended or multi-phase form. For the purposes of the present disclosure, the term "liquid" also encompasses any types of solid-state dispersions in liquids. Furthermore, multi-phase compositions used in the context of the present disclosure are understood to mean compositions which have at least 2 different phases with a phase separation and in which the phases are arranged horizontally, in other words one above the other, or vertically, that is to say next to one another. Application of such compositions can take place, for example, as a solid stick, soft solid, cream/wax, or roll-on.

Creamy, pasty and liquid compositions as contemplated herein can be used, for example, in pump, spray or squeeze dispensers, particularly in multi-chamber pump, multi-chamber spray or multi-changer squeeze dispensers. The packaging can be opaque, transparent or translucent and may contain no propellants.

The composition of the present disclosure may also be packaged in a tube (for example made from plastic, polymers, metal, combined laminates and so on), ajar (for example made from wood, natural fibers, paper, cardboard, metal, plastic, polymers, combined laminates, glass and so on), a stick case (for example made from plastic, polymers, paper, card board, combined laminates, glass and so on), or a dispenser (for example made from plastic, polymers, paper, card board, combined laminates, glass and so on).

The viscosity of a composition for use in a roll-on product is advantageously at least about 300 mPa·s; preferably at least about 1,000 mPa·s, more preferably at least about 5,000 mPa·s, and most preferably at least about 10,000 mPa·s. The viscosity of a composition for use in a cream product is advantageously at least about 5,000 mPa·s; preferably at least about 7,000 mPa·s, more preferably at least about 10,000 mPa·s.

The anhydrous cosmetic composition is the composition disclosed herein. Therefore, all features of the anhydrous cosmetic composition disclosed herein also apply mutatis mutandis to the preferred features of the cosmetic product.

The term "improvement of sensory properties of anhydrous deodorant composition", is understood to mean, in particular, the improved dry skin feeling that the composition leaves after application on the skin.

The present disclosure may also be defined by the following statements. The statements are not intended to be limiting but provide examples of preferred features of the present disclosure.

A deodorant cosmetic composition comprising calcium silicate and sodium bicarbonate.

The deodorant cosmetic composition as contemplated herein, wherein the composition is anhydrous (a definition of the term "anhydrous" is provided above).

The deodorant cosmetic composition as contemplated herein, wherein the calcium silicate is present in particulate form, wherein the particles have a median particle size (D50) ranging from about 0.5 to about 100 microns (particle size measurement techniques are provided above).

The deodorant cosmetic composition as contemplated herein, wherein the particles have a median particle size (D50) from about 0.5 to about 50 microns.

The deodorant cosmetic composition as contemplated herein, wherein the particles have a median particle size (D50) ranging from about 1 to about 20 microns; preferably from about 1 to about 15 microns; more preferably from about 5 to about 15 microns.

The deodorant cosmetic composition a as contemplated herein, wherein the calcium silicate has a bulk density ranging from about 50 kg/m$^3$ to about 200 kg/m$^3$.

The deodorant cosmetic composition as contemplated herein, wherein the calcium silicate has a bulk density ranging from about 75 kg/m$^3$ to about 180 kg/m$^3$.

The deodorant cosmetic composition as contemplated herein, wherein the calcium silicate has a BET surface area particle size ranging from about 50 kg/m$^3$ to about 200 kg/m$^3$, preferably from about 75 kg/m$^3$ to about 180 kg/m$^3$.

The deodorant cosmetic composition as contemplated herein, wherein the amount of the baking soda ranges from about 3 to about 25 wt %, relative to the total weight of the cosmetic composition; preferably from about 5 to about 20 wt %.

The deodorant cosmetic composition as contemplated herein, wherein the amount of the baking soda ranges from about 8 to about 18 wt %, preferably from about 10 to about 15 wt %.

The deodorant cosmetic composition as contemplated herein, wherein the amount of the calcium silicate ranges from about 0.1 to about 20 wt %, relative to the total weight of the cosmetic composition; preferably from about 0.5 to about 15 wt %.

The deodorant cosmetic composition as contemplated herein, wherein the amount of the calcium silicate ranges from about 1 to about 10 wt %, preferably from about 1 to about 8 wt %.

The deodorant cosmetic composition as contemplated herein, wherein the composition further comprises at least one emollient.

The deodorant cosmetic composition as contemplated herein, wherein the composition further comprises one, two or three or more emollients.

The deodorant cosmetic composition as contemplated herein, wherein the one or each emollient is selected from coco-caprylate, caprylic/capric triglyceride, cocoglycerides, C9-12 Alkane, and coco-caprylate/caprate.

The deodorant cosmetic composition as contemplated herein, wherein the composition further comprises at least one structurant.

The deodorant cosmetic composition as contemplated herein, wherein the composition further comprises one, two or three structurants.

The deodorant cosmetic composition as contemplated herein, wherein the or each structurant is selected from Cocos Nucifera (Coconut) Oil, Butyrospermum Parkii (Shea) Butter, Stearyl Alcohol, Hydrogenated Castor Oil, Hydrogenated Rapeseed Oil, Cocoglycerides and Myristyl Myristate.

The deodorant cosmetic composition as contemplated herein \, wherein the composition further comprises at least one water-absorbing component.

The deodorant cosmetic composition as contemplated herein, wherein the water-absorbing component is a starch.

The deodorant cosmetic composition as contemplated herein, wherein the starch is Zea Mays (Corn) Starch, Arrow Root Starch, Tapioca Starch, Rice Starch, or Potato Starch.

The deodorant cosmetic composition according to any preceding Statement, wherein the composition comprises no water-soluble aluminum and/or aluminum zirconium salts.

The deodorant cosmetic composition as contemplated herein, wherein the composition further comprises at least one deodorant active ingredient.

The deodorant cosmetic composition as contemplated herein, wherein the at least one deodorant active ingredient is not an aluminum and/or aluminum zirconium salt.

The deodorant cosmetic composition as contemplated herein, wherein the or each deodorant active ingredient is a natural oil, preferably an essential oil.

The deodorant cosmetic composition as contemplated herein, wherein the deodorant active ingredient is selected from Rosmarinus Officinalis (Rosemary) Oil, Clove oil, Thyme oil, Cinnamon oil, Laurel oil, any Oil from the fruits of the Citrus family, and mixtures thereof.

The deodorant cosmetic composition as contemplated herein, wherein the deodorant active ingredient comprises calcium carbonate.

The deodorant cosmetic composition as contemplated herein, wherein the deodorant active ingredient comprises precipitated calcium carbonate.

The deodorant cosmetic composition as contemplated herein, wherein the composition further comprises at least one emulsifier.

The deodorant cosmetic composition as contemplated herein, wherein the at least one emulsifier is based on cetearyl alcohol, cetearyl glucoside or a mixture thereof.

A cosmetic product comprising the deodorant cosmetic composition as contemplated herein.

A cosmetic product as contemplated herein, which is a stick.

A cosmetic product as contemplated herein, which is a roll-on.

A cosmetic product as contemplated herein, which is a cream, paste, or a wax.

A method of using a deodorant cosmetic composition or a cosmetic as contemplated herein, the method comprising using the cosmetic composition to improve the sensory properties of deodorant compositions.

The method as contemplated herein wherein using the cosmetic composition comprises using the deodorant cosmetic composition to reduce body odor released by perspiration.

Use of a deodorant cosmetic composition as contemplated herein or a cosmetic product as contemplated herein, to prevent and/or reduce body odor.

A non-therapeutic cosmetic method for preventing and/or reducing body odor, in which the deodorant cosmetic composition as contemplated herein or the cosmetic product as contemplated herein, is applied to the skin, in particular, to the skin of the armpits, and left on the skin; particularly for at least about 1 hour, preferably for at least about 2 hours, more preferably for at least about 4 hours, yet more preferably, for at least about 6 hours, even more preferably for at least about 24 hours.

The following examples explain the present disclosure without limiting it.

Examples

The smell reduction of reconstructed Body Odor models out of body odor constituents by contact with the cosmetic products was tested.

Method of Sample Preparation

Filter papers were dried for 24 hours at 37° C. (against inherent smell). The dried papers were saturated with 0.3 ml of the particular test solution and afterwards dried for 1 hour at room temperature. Each filter was contaminated with 15 µl of the artificial body odor. The contaminated filter papers were stored at room temperature for 24 hours in 1 litre screw-top jars.

Afterwards the odor was evaluated by trained sniffers. The sniffers scored the samples based on a score of 0 to 4: score of 0=no odor; score of 4=intense odor.

Examples

One sulphanyl-alcohol based sweat mixture (sweat solution 1), and two volatile acid-based sweat mixtures (sweat solutions 2 and 3) were tested. One acid-based sweat solution (sweat solution 2) was stored at room temperature, the other (sweat solution 3) was stored for 24 hours at 37° C. before evaluation.

The calcium silicate used in all the tests was Zeofree® 250 (available from Evonik, as described in further detail above).

Using a water-free cream as a base, the following were tested:
1. Standard sweat odor without cosmetic product
2. Cream without additives
3. Cream with Calcium Silicate 3%/Sodium Bicarbonate 15%
4. Cream with Calcium Silicate 5%/Sodium Bicarbonate 0%

The scores from the tests were as follows.

TABLE 5

Sweat solution 1 - containing sulfur compounds

| | Baking Soda | Calcium Silicate | Study 1 11 sniffers | Study 2 11 sniffers |
|---|---|---|---|---|
| 1 | 0 | 0 | 4.00 | 4.00 |
| 2 | 0 | 0 | 3.36 | |
| 3 | 15 | 3 | 2.73 | |
| 4 | 0 | 5 | | 2.86 |

TABLE 6

Sweat solution 2 - containing acid compounds I

| | Baking Soda | Calcium Silicate | Study 1 11 sniffers | Study 2 11 sniffers |
|---|---|---|---|---|
| 1 | 0 | 0 | 3.77 | 3.77 |
| 2 | 0 | 0 | 2.27 | |
| 3 | 15 | 3 | 1.45 | |
| 4 | 0 | 5 | | 1.86 |

TABLE 7

Sweat solution 3 - containing acid compounds II

| | Baking Soda | Calcium Silicate | Study 1 11 sniffers | Study 2 11 sniffers |
|---|---|---|---|---|
| 1 | 0 | 0 | 3.45 | 3.59 |
| 2 | 0 | 0 | 2.18 | |

TABLE 7-continued

Sweat solution 3 - containing acid compounds II

| | Baking Soda | Calcium Silicate | Study 1 11 sniffers | Study 2 11 sniffers |
|---|---|---|---|---|
| 3 | 15 | 3 | 1.27 | |
| 4 | 0 | 5 | | 1.36 |

DISCUSSION

It can be seen that the addition of calcium silicate has a good effect on sulfanylalcohols and acids, and the combination with baking soda is particularly beneficial.

Thus, it can be seen that the use of calcium silicate according to a preferred aspect of the present disclosure, in combination with sodium bicarbonate provides unexpected advantages during production in terms of viscosity and sedimentation.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A deodorant cosmetic composition consisting of calcium silicate in an amount of from about 1 to about 8 weight percent, based on a total weight of the deodorant cosmetic composition, sodium bicarbonate in an amount of from about 10 to about 15 weight percent, based on the total weight of the deodorant cosmetic composition, coconut oil, shea butter, stearyl alcohol, hydrogenated castor oil, hydrogenated rapeseed oil, corn starch, arrow root starch, calcium carbonate, coco-caprylate, caprylic/capric triglyceride, C9-C12 alkane, coco-caprylate/caprate, cocoglycerides, myristyl myristate, perfume, and rosemary oil.

2. The deodorant cosmetic composition according to claim 1, wherein the calcium silicate is present in the deodorant cosmetic composition in an amount of about 3 weight percent, based on the total weight of the deodorant cosmetic composition, and the sodium bicarbonate is present in the deodorant cosmetic composition in an amount of about 15 weight percent, based on the total weight of the deodorant cosmetic composition.

3. A method comprising the step of using a deodorant cosmetic composition according to claim 1 to prevent and/or reduce body odor.

4. The method of claim 3, the method further comprising the steps of: applying the deodorant cosmetic composition to skin, and leaving the deodorant cosmetic composition on the skin for at least 1 hour.

* * * * *